United States Patent
Sanchez et al.

(10) Patent No.: US 10,192,734 B2
(45) Date of Patent: Jan. 29, 2019

(54) SHORT INORGANIC TRISILYLAMINE-BASED POLYSILAZANES FOR THIN FILM DEPOSITION

(71) Applicants: Air Liquide Advanced Materials, Inc., Branchburg, NJ (US); L'Air Liquide, Société Anonyme pour l;etude et l'Exploitation des Procédés Georges Claude, Paris (FR); Air Liquide Advanced Materials LLC, Branchburg, PA (US)

(72) Inventors: Antonio Sanchez, Tsukuba (JP); Gennadiy Itov, Flemington, NJ (US); Reno Pesaresi, Easton, PA (US); Jean-Marc Girard, Versailles (FR); Peng Zhang, Montvale, NJ (US); Manish Khandelwal, Somerset, NJ (US)

(73) Assignees: L'Air Liquide, Société Anonyme pour l'Etude et l'Exploration des Procédés Georges Claude, Paris (FR); Air Liquide Advanced Materials, Inc., Branchburg, NJ (US); Air Liquide Advanced Materials LLC, Branchburg, NJ (US)

( * ) Notice: Subject to any disclaimer, the term of this patent is extended or adjusted under 35 U.S.C. 154(b) by 0 days.

(21) Appl. No.: 15/661,576

(22) Filed: Jul. 27, 2017

(65) Prior Publication Data

US 2017/0323783 A1    Nov. 9, 2017

Related U.S. Application Data

(60) Provisional application No. 62/432,666, filed on Dec. 11, 2016.

(51) Int. Cl.
*H01L 21/02* (2006.01)
*C07F 7/10* (2006.01)
(Continued)

(52) U.S. Cl.
CPC ........ *H01L 21/02211* (2013.01); *C07F 7/10* (2013.01); *C23C 16/345* (2013.01);
(Continued)

(58) Field of Classification Search
CPC .......... H01L 21/02211; H01L 21/0228; H01L 21/0217; H01L 21/02164; H01L 21/02274;
(Continued)

(56) References Cited

U.S. PATENT DOCUMENTS 4,675,424 A   6/1987   King, III
5,413,813 A   5/1995   Cruse et al.
(Continued)

FOREIGN PATENT DOCUMENTS

DE   1 158 972   12/1964
EP   2 000 561   12/2008
(Continued)

OTHER PUBLICATIONS

Andreev, A.A. et al., "Direct electrophilic silylation of terminal alkynes," Organic Letters 2004, vol. 6, No. 3, 421-424 and SI1-SI5.
(Continued)

*Primary Examiner* — Jasmine Clark
(74) *Attorney, Agent, or Firm* — Patricia E. McQueeney

(57) ABSTRACT

Si-containing film forming compositions comprising Si—C free and volatile silazane-containing precursors are disclosed. The compositions may be used to deposit high purity thin films. The Si—C free and volatile silazane-containing precursors have the formulae:

$[(SiR_3)_2NSiH_2]_m$—$NH_{2-m}$—C≡N, with $m=1$ or 2;  (a)

$[(SiR_3)_2NSiH_2]_n$—$NL_{3-n}$, with $n=2$ or 3;  (b)

(Continued)

$(SiH_3)_2NSiH_2$—O—$SiH_2N(SiH_3)_2$; and (c)

$(SiR'_3)_2N$—$SiH_2$—$N(SiR'_3)_2$; (d)

with each R independently selected from H, a dialkylamino group, or an amidinate; each R' independently selected from H, a dialkylamino group, or an amidinate, with the provision that all R' are not H; and L is selected from H or a $C_1$-$C_6$ hydrocarbyl group.

11 Claims, 1 Drawing Sheet

(51) Int. Cl.
  C23C 16/34 (2006.01)
  C23C 16/40 (2006.01)
(52) U.S. Cl.
  CPC ........ *C23C 16/402* (2013.01); *H01L 21/0217* (2013.01); *H01L 21/0228* (2013.01); *H01L 21/02164* (2013.01); *H01L 21/02274* (2013.01); *H01L 21/02222* (2013.01)
(58) Field of Classification Search
  CPC ............. H01L 21/02208; C23C 16/345; C23C 16/402; C07F 7/10
  See application file for complete search history.

(56) References Cited

U.S. PATENT DOCUMENTS

| | | | |
|---|---|---|---|
| 5,874,368 | A | 2/1999 | Laxman et al. |
| 7,638,645 | B2 | 12/2009 | Gordon et al. |
| 7,838,329 | B2 | 11/2010 | Hunks et al. |
| 8,357,430 | B2 | 1/2013 | Dussarrat et al. |
| 8,409,513 | B2 | 4/2013 | Miller |
| 8,771,807 | B2 * | 7/2014 | Xiao .................. C07F 7/025 427/578 |
| 2005/0070717 | A1 | 3/2005 | Wasserscheid et al. |
| 2005/0181633 | A1 | 8/2005 | Hochberg et al. |
| 2006/0222583 | A1 | 10/2006 | Hazeltine |
| 2007/0010072 | A1 | 1/2007 | Bailey et al. |
| 2008/0045723 | A1 | 2/2008 | Cassol et al. |
| 2008/0241575 | A1 | 10/2008 | Lavoie et al. |
| 2008/0268642 | A1 | 10/2008 | Yanagita et al. |
| 2009/0075490 | A1 | 3/2009 | Dussarrat |
| 2009/0111284 | A1 * | 4/2009 | Wang .................. C23C 16/345 438/791 |
| 2009/0137100 | A1 | 5/2009 | Xiao et al. |
| 2009/0256127 | A1 | 10/2009 | Feist et al. |
| 2009/0291872 | A1 | 11/2009 | Bara et al. |
| 2009/0291874 | A1 | 11/2009 | Bara et al. |
| 2009/0299084 | A1 | 12/2009 | Okubo et al. |
| 2010/0104755 | A1 | 4/2010 | Dussarrat et al. |
| 2010/0221428 | A1 | 9/2010 | Dussarrat |
| 2011/0129616 | A1 | 6/2011 | Ingle et al. |
| 2012/0017934 | A1 | 1/2012 | Kumon et al. |
| 2012/0058282 | A1 | 3/2012 | Hong et al. |
| 2012/0213940 | A1 | 8/2012 | Mallick |
| 2012/0220139 | A1 | 8/2012 | Lee et al. |
| 2013/0089487 | A1 | 4/2013 | Ritter, III |
| 2013/0143018 | A1 | 6/2013 | Tan et al. |
| 2013/0189854 | A1 | 7/2013 | Hausmann et al. |
| 2013/0224097 | A1 | 8/2013 | Miller |
| 2013/0323435 | A1 | 12/2013 | Xiao et al. |
| 2014/0051264 | A1 | 2/2014 | Mallick et al. |
| 2014/0158580 | A1 | 6/2014 | Xiao et al. |
| 2014/0193953 | A1 | 7/2014 | Lavoie |
| 2015/0376211 | A1 | 12/2015 | Girard et al. |
| 2016/0049293 | A1 | 2/2016 | Li et al. |
| 2016/0225616 | A1 | 8/2016 | Li et al. |

FOREIGN PATENT DOCUMENTS

| | | |
|---|---|---|
| KR | 10 2012 0024473 | 3/2012 |
| KR | 10 2012 0099270 | 9/2012 |
| KR | 10 2013 0135793 | 12/2013 |
| KR | 10 2014 0057908 | 5/2014 |
| WO | WO 2006 136584 | 12/2006 |
| WO | WO 2007 008705 | 1/2007 |
| WO | WO 2009 087609 | 7/2009 |
| WO | WO 2011 056519 | 5/2011 |
| WO | WO 2015 047914 | 9/2014 |
| WO | WO 2015 190749 | 12/2015 |
| WO | WO 2016 065219 | 4/2016 |
| WO | WO 2016 065221 | 4/2016 |
| WO | WO 2016 160990 | 10/2016 |
| WO | WO 2017 070192 | 4/2017 |
| WO | WO 2017 147150 | 8/2017 |

OTHER PUBLICATIONS

Cradock, S. et al., "Reactions of tin(IV) chloride with silyl compounds. I. Reactions with inorganic silyl compounds," Journal of the Chemical Society Dalton Transactions, Jan. 1975, 1624-1628.
Felch, S.B. et al., "Plasma doping for the fabrication of ultra-shallow junctions," Surface and Coatings Technology 156 (2002) 229-236.
Godleski, S.A., et al., "MNDO study of phosphine- and amine-substituted silicenium ions", Tetrahedron Letter (1982), 23(43) 4453-3356.
Ishii, K. et al., "Growth of polycrystalline hexagonal-close-packed Co films on glass substrates from low kinetic energy vapor," Journal of Vacuum Science & Technology A 16 (1998), 759-762.
Lee, J. et al., "A hydrogen gas sensor employing vertically aligned $TiO_2$ nanotube arrays," Sensors and Actuators B 160 (2011) 1494-1498.
Norman, A.D. et al., "Reaction of silylphosphine with ammonia," Inorganic Chemistry, vol. 18, No. 6, 1979, 1594-1597.
Scantlin, W.M., et al., "The borane-catalyzed condensation of trisilazane and N-methyldisilazane", Inorganic Chemistry (1972), 11(12), 3028-2084.
Scantlin, W.M., et al., "Pentaborane(9)-catalyzed condensation of silylamines", Journal of the Chemical Society D: Chemical Communications (1971), (20), 1246.
Schmidbauer, H. et al., "Difference in reactivity of 1,4-disilabutane and n-tetrasilane towards secondary amines," Z. Naturforsch. 45b, 1990, 1679-1863.
Sommer, L.H. et al, "Stereochemistry of asymmetric silicon. XVI. Transition metal catalyzed substitute reactions of optically active organosilicon hydrides," Journal of the American Chemical Society, 91:25, Dec. 3, 1969, 7061-7067.
Toh, C.K. et al., "Ruthenium carbonyl-catalysed Si-heteroatom X coupling (X=S, O, N)," Journal of Organometallic Chemistry 717 (2012) 9-13.
International Search Report and Written Opinion for related PCT/US2014/056618, dated Dec. 12, 2014.
International Search Report and Written Opinion for related PCT/US2016/025010, dated Jul. 15, 2016.
International Search Report and Written Opinion for related PCT/US2016/037006, dated Sep. 12, 2016.
International Search Report and Written Opinion for related PCT/US2016/037013, dated Sep. 12, 2016.
International Search Report and Written Opinion for corresponding PCT/US2017/065506, dated Mar. 27, 2018.
Aylett, B.J. et al., "Silicon-nitrogen compounds. Part VI. The preparation and properties of disilazane," J. Chem. Soc. (A), 1969, 639-642.
Breed, L.W. et al., "Functionally substituted trisilylamine derivatives," J. Organometal. Chem., 11 (1968), 447-457.
Iida, A. et al., "Anilinosilanes/TBAF catalyst: mild and powerful agent for the silylations of sterically hindered alcohols," Synthesis 2005, No. 16, 2677-2682.

(56) References Cited

OTHER PUBLICATIONS

Königs, C.D.F. et al., "Catalytic dehydrogenative Si—N coupling of pyrroles, indoles, carbazoles as well as anilines with hydrosilanes without added base," Chem. Commun., 2013, 49, 1506-1508.

* cited by examiner

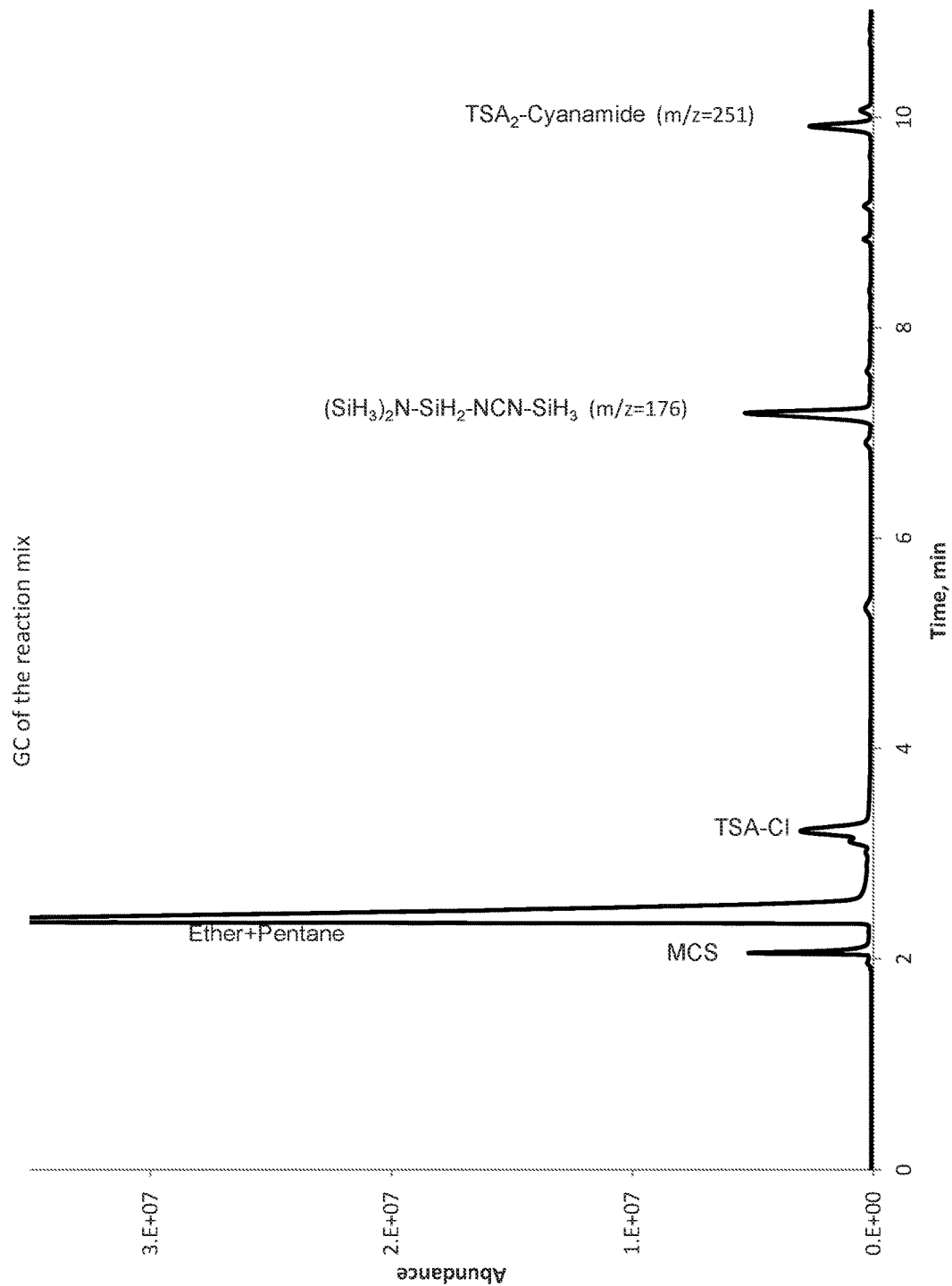

SHORT INORGANIC TRISILYLAMINE-BASED POLYSILAZANES FOR THIN FILM DEPOSITION

CROSS REFERENCE TO RELATED APPLICATIONS

The present application claims the benefit of U.S. Provisional Application No. 62/432,666 filed Dec. 11, 2016, herein incorporated by reference in its entirety for all purposes.

TECHNICAL FIELD

Si-containing film forming compositions comprising Si—C free and volatile silazane-containing precursors are disclosed. The compositions may be used to deposit high purity thin films.

BACKGROUND

With the scaling down of semiconductor devices, new materials are required. Common materials, like silicon nitride or silicon oxide, need to be deposited in increasingly stringent conditions. For instance, there is a general trend for silicon nitride deposition by Chemical Vapor Deposition (CVD) or Atomic Layer Deposition (ALD) at the lowest possible temperature, while keeping a high deposition rate a high film quality. For such processes, the precursor molecule plays a critical role to obtain high quality films with low impurities, and with the suitable conformality properties (from highly conformal for some application, to bottom up fills for other applications).

WO2015/047914 to Sanchez et al. discloses halogen free amine substituted trisilylamine and tridisilylamine compounds and a method of their preparation via dehydrogenative coupling between the corresponding unsubstituted trisilylamines and amines catalyzed by transition metal catalysts.

US2015/376211 to Girard et al. discloses mono-substituted TSA precursors Si-containing film forming compositions.

US2016/0049293 to Li et al. discloses a method and composition comprising same for sealing the pores of a porous low dielectric constant layer by providing an additional thin dielectric film.

US2016/0225616 to Li et al. discloses an apparatus comprising a plurality of silicon-containing layers wherein the silicon-containing layers are selected from a silicon oxide and a silicon nitride layer or film.

WO2016/065221 to Lei et al. discloses compositions and methods using same for forming a silicon-containing film or material.

Molecules lacking Si—C direct bonds are known to yield purer films than molecules having such direct bonds, owing to the low reactivity and high thermal stability of the Si—C bond.

Additionally, silanes having alkoxy groups rarely exhibit proper self limiting growth by atomic layer deposition, and do not allow the formation of silicon nitride films as the oxygen normally remains in the film, and hence are not as versatile as aminosilanes having Si—N bonds in terms of possible applications for thin film deposition. However, while an alkoxy group doesn't appear as a suitable functional group for surface reaction in atomic layer deposition, Si—C free molecules having a Si—O—Si (siloxane) bridge have been proposed and may be used.

Typical Si—C-free silane precursors that have been proposed and used industrially for silicon oxide and silicon nitride thin film deposition are
- a—halosilanes, such as dichlorosilane, monochlorosilane, hexachlorodisilane, octachlorotriisilane, di-iodo silane, pentachlorodisilane, etc.
- b—perhydrido(poly)silanes such as SiH4, Si2H6 or Si3H8
- c—Amino silanes having the general formula SiHx(NR1R2)4-x, such as bis-diethylaminosilanes, tris-dimethylaminosilane, diisopropylaminosilane, bis(ethylmethylamino)silane, tetrakis(ethylamino)silane
- d—Amino-disilanes, such as hexakis(ethylamino)disilane, diisopropylaminosilane, diethylaminodisilane.
- e—Siloxane, such as disiloxane, hexachlorodisiloxane
- f—Trisilylamine, which may be used for a variety of deposition processes such as flowable CVD, thermal low pressure CVD, plasma enhanced CVD, ALD, and plasma enhanced ALD.
- g—More recently, other silicon-rich molecules have been proposed such as TSA-Cl or BDSASi. BDSASi for instance has been reported to yield high growth per cycle SiN by PEALD.

However, molecules enabling higher growth rates at low temperature, whether by ALD, CVD, flowable CVD or other forms of vapor deposition, while maintaining high film purity are still sought to further gain process productivity, or enable depositing in lower temperature conditions than usual precursors.

SUMMARY

Silicon-containing film forming compositions are disclosed. The silicon-containing film forming compositions comprise a precursor selected from the group consisting of:

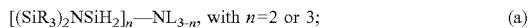  (a)

$[(SiR_3)_2NSiH_2]_n$—NL$_{3-n}$, with $n=2$ or 3;

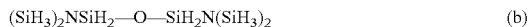  (b)

$(SiH_3)_2NSiH_2$—O—$SiH_2N(SiH_3)_2$

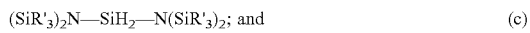  (c)

$(SiR'_3)_2N$—$SiH_2$—$N(SiR'_3)_2$; and

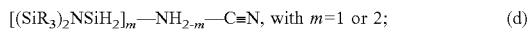  (d)

$[(SiR_3)_2NSiH_2]_m$—$NH_{2-m}$—C≡N, with $m=1$ or 2;

wherein
each R is independently selected from H, a dialkylamino group having the formula —$NR^1R^2$, or an amidinate,
Each R' is independently selected from H, a dialkylamino group having the formula —$NR^1R^2$, or an amidinate, with the provision that all R' are not H,
$R^1$ and $R^2$ are independently selected from H or a C1-C12 hydrocarbyl group, with the provision that $R^1$ and $R^2$ cannot be simultaneously equal to H, and that if $R^1$ is H, then $R^2$ is a $C_2$-C12 hydrocarbyl group, and $NR^1R^2$ may together form an N-containing heterocyclic ligand, and
L is selected from H or a $C_1$-$C_6$ hydrocarbyl group.

The disclosed Silicon-containing film forming compositions may comprise one or more of the following aspects:
- the precursor being $[(SiH_3)_2NSiH_2]_2NH$;
- the precursor being $[(SiH_3)_2NSiH_2]_3N$;
- the precursor being $(SiH_3)_2N$—$SiH_2$—$N(SiH_3)(SiH_2NR^1R^2)$;
- the precursor being $(SiH_3)_2NSiH_2$—O—$SiH_2N(SiH_3)_2$;
- the precursor being $[(SiH_3)_2NSiH_2]$—NH—C≡N;
- the precursor being $[(SiH_3)_2NSiH_2]_2N$—C≡N;
- the precursor being $(SiH_3)_2N$—$SiH_2$—$N(SiH_3)(SiH_2NMe_2)$;

the precursor being (SiH$_3$)$_2$N—SiH$_2$—N(SiH$_3$)(SiH$_2$NEt$_2$);
the precursor being (SiH$_3$)$_2$N—SiH$_2$—N(SiH$_3$)(SiH$_2$NEtMe);
the precursor being (SiH$_3$)$_2$N—SiH$_2$—N(SiH$_3$)(SiH$_2$NiPr$_2$);
the precursor being (SiH$_3$)$_2$N—SiH$_2$—N(SiH$_3$)(SiH$_2$NtBu$_2$);
the precursor being (SiH$_3$)$_2$N—SiH$_2$—N(SiH$_3$)(SiH$_2$NnBu$_2$);
the precursor being (SiH$_3$)$_2$N—SiH$_2$—N(SiH$_3$)(SiH$_2$NsecBu$_2$);
the precursor being (SiH$_3$)$_2$N—SiH$_2$—N(SiH$_3$)(SiH$_2$NHtBu);
the Si-containing film forming composition comprising between approximately 95% w/w and approximately 100% w/w of the precursor;
the Si-containing film forming composition comprising between approximately 5% w/w and approximately 50% w/w of the precursor;
the Si-containing film forming composition comprising between approximately 0 ppbw and approximately 500 ppbw Al;
the Si-containing film forming composition comprising between approximately 0 ppbw and approximately 500 ppbw As;
the Si-containing film forming composition comprising between approximately 0 ppbw and approximately 500 ppbw Ba;
the Si-containing film forming composition comprising between approximately 0 ppbw and approximately 500 ppbw Be;
the Si-containing film forming composition comprising between approximately 0 ppbw and approximately 500 ppbw Bi;
the Si-containing film forming composition comprising between approximately 0 ppbw and approximately 500 ppbw Cd;
the Si-containing film forming composition comprising between approximately 0 ppbw and approximately 500 ppbw Ca;
the Si-containing film forming composition comprising between approximately 0 ppbw and approximately 500 ppbw Cr;
the Si-containing film forming composition comprising between approximately 0 ppbw and approximately 500 ppbw Co;
the Si-containing film forming composition comprising between approximately 0 ppbw and approximately 500 ppbw Cu;
the Si-containing film forming composition comprising between approximately 0 ppbw and approximately 500 ppbw Ga;
the Si-containing film forming composition comprising between approximately 0 ppbw and approximately 500 ppbw Ge;
the Si-containing film forming composition comprising between approximately 0 ppbw and approximately 500 ppbw Hf;
the Si-containing film forming composition comprising between approximately 0 ppbw and approximately 500 ppbw Zr;
the Si-containing film forming composition comprising between approximately 0 ppbw and approximately 500 ppbw In;
the Si-containing film forming composition comprising between approximately 0 ppbw and approximately 500 ppbw Fe;
the Si-containing film forming composition comprising between approximately 0 ppbw and approximately 500 ppbw Pb;
the Si-containing film forming composition comprising between approximately 0 ppbw and approximately 500 ppbw Li;
the Si-containing film forming composition comprising between approximately 0 ppbw and approximately 500 ppbw Mg;
the Si-containing film forming composition comprising between approximately 0 ppbw and approximately 500 ppbw Mn;
the Si-containing film forming composition comprising between approximately 0 ppbw and approximately 500 ppbw W;
the Si-containing film forming composition comprising between approximately 0 ppbw and approximately 500 ppbw Ni;
the Si-containing film forming composition comprising between approximately 0 ppbw and approximately 500 ppbw K;
the o Si-containing film forming composition comprising between approximately 0 ppbw and approximately 500 ppbw Na;
the Si-containing film forming composition comprising between approximately 0 ppbw and approximately 500 ppbw Sr;
the Si-containing film forming composition comprising between approximately 0 ppbw and approximately 500 ppbw Th;
the Si-containing film forming composition comprising between approximately 0 ppbw and approximately 500 ppbw Sn;
the Si-containing film forming composition comprising between approximately 0 ppbw and approximately 500 ppbw Ti;
the Si-containing film forming composition comprising between approximately 0 ppbw and approximately 500 ppbw U;
the Si-containing film forming composition comprising between approximately 0 ppbw and approximately 500 ppbw V;
the Si-containing film forming composition comprising between approximately 0 ppbw and approximately 500 ppbw Zn;
the Si-containing film forming organosilane composition comprising between approximately 0 ppmw and approximately 500 ppmw Cl;
the Si-containing film forming composition comprising between approximately 0 ppmw and approximately 500 ppmw Br;
the Si-containing film forming composition comprising between approximately 0 ppmw and approximately 500 ppmw I;
the Si-containing film forming composition comprising between approximately 0.0% w/w and 0.1% w/w TSA;
the Si-containing film forming composition comprising between approximately 0.0% w/w and 0.1% w/w (SiH$_3$)$_2$—N—SiH$_2$X, wherein X is Cl, Br, or I;
the Si-containing film forming composition comprising between approximately 0.0% w/w and 0.1% w/w (SiH$_3$)$_2$—N—SiHX$_2$, wherein X is Cl, Br, or I;
the Si-containing film forming composition comprising between approximately 0.0% w/w and 0.1% w/w SiH$_4$;

the Si-containing film forming composition comprising between approximately 0.0% w/w and 0.1% w/w SiH$_3$X, wherein X is Cl, Br, or I;

the Si-containing film forming composition comprising between approximately 0.0% w/w and 0.1% w/w SiH$_2$X$_2$, wherein X is Cl, Br, or I;

the Si-containing film forming composition comprising between approximately 0.0% w/w and 0.1% w/w SnX$_2$, wherein X is Cl, Br, or I;

the Si-containing film forming composition comprising between approximately 0.0% w/w and 0.1% w/w SnX$_4$, wherein X is Cl, Br, or I;

the Si-containing film forming composition comprising between approximately 0.0% w/w and 0.1% w/w HX, wherein X is Cl, Br, or I;

the Si-containing film forming composition comprising between approximately 0.0% w/w and 0.1% w/w NH$_3$;

the Si-containing film forming composition comprising between approximately 0.0% w/w and 0.1% w/w NH$_4$X, wherein X is Cl, Br, or I;

the Si-containing film forming composition comprising between approximately 0.0% w/w and 0.1% w/w ROH, wherein R is C1-C4 alkyl group;

the Si-containing film forming composition comprising between approximately 0.0% w/w and 0.1% w/w NH$_2$R, wherein R is a C1-C4 alkyl group;

the Si-containing film forming composition comprising between approximately 0.0% w/w and 0.1% w/w NR$_2$H, wherein R is a C1-C4 alkyl group;

the Si-containing film forming composition comprising between approximately 0.0% w/w and 0.1% w/w HN=R, wherein R is a C1-C4 alkyl group;

the Si-containing film forming composition comprising between approximately 0.0% w/w and 0.1% w/w tetrahydrofuran (THF);

the Si-containing film forming composition comprising between approximately 0.0% w/w and 0.1% w/w ether;

the Si-containing film forming composition comprising between approximately 0.0% w/w and 0.1% w/w pentane;

the Si-containing film forming composition comprising between approximately 0.0% w/w and 0.1% w/w cyclohexane;

the Si-containing film forming composition comprising between approximately 0.0% w/w and 0.1% w/w heptane; or the Si-containing film forming composition comprising between approximately 0.0% w/w and 0.1% w/w toluene.

Methods of depositing silicon-containing films on a substrate by chemical vapor deposition methods are disclosed. The vapor of any of the Si-containing film forming compositions disclosed above is introduced into a reactor containing a substrate. At least part of the precursor is deposited onto the substrate to form the silicon-containing film on the substrate using a chemical vapor deposition process. The disclosed method may include one or more of the following aspects:

the chemical vapor deposition method being an atomic layer deposition process;

the chemical vapor deposition method being a plasma enhanced atomic layer deposition process;

introducing into the reactor a vapor comprising a second precursor;

an element of the second precursor being selected from the group consisting of group 2, group 13, group 14, transition metal, lanthanides, and combinations thereof;

the element of the second precursor being selected from As, B, P, Si, Ge, Al, Zr, Hf, Ti, Nb, Ta, or lanthanides;

introducing a reactant into the reactor;

the reactant being selected from the group consisting of O$_2$, O$_3$, H$_2$O, H$_2$O$_2$, NO, NO$_2$, a carboxylic acid, an alcohol, a diol, radicals thereof, and combinations thereof;

the reactant being plasma treated oxygen;

the silicon-containing film being a silicon oxide film;

the silicon-containing film being a silicon nitride film;

the substrate being a silicon wafer;

the substrate being glass;

the substrate being an organic material;

thermal annealing the Si-containing layer;

thermal annealing the Si-containing layer under a reactive atmosphere;

UV curing the Si-containing layer; and

Electron beam curing the Si-containing layer.

Notation and Nomenclature

Certain abbreviations, symbols, and terms are used throughout the following description and claims, and include:

As used herein, the indefinite article "a" or "an" means one or more.

As used herein, the terms "approximately" or "about" mean±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula MR$^1_x$ (NR$^2$R$^3$)$_{(4-x)}$, where x is 2 or 3, the two or three R$^1$ groups may, but need not be identical to each other or to R$^2$ or to R$^3$. Further, it should be understood that unless specifically stated otherwise, values of R groups are independent of each other when used in different formulas.

As used herein, the term "hydrocarbyl group" refers to a functional group containing carbon and hydrogen; the term "alkyl group" refers to saturated functional groups containing exclusively carbon and hydrogen atoms. The hydrocarbyl group may be saturated or unsaturated. Either term refers to linear, branched, or cyclic groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, "C-free" means starting reactant has no Si—C bond.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPr" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the term "amyl" refers to an amyl or pentyl group (i.e., a C5 alkyl group); the term "tAmyl" refers to a tert-amyl group, also known as 1,1-dimethylpropyl.

The term "halide" refers to the halogen anions $F^-$, $Cl^-$, $Br^-$, and $I^-$; the term "silyl" refers to a $R_3Si—$ ligand, wherein each R is independently H or a C1-C4 alkyl group. The term "halide salt" refers to an ionic compound containing a halide ion.

As used herein, the abbreviation "$N^{R,R'}R''$-amd" or $N^R R''$-amd when $R=R'$ refers to the amidinate ligand [R—N—C(R'')=N—R'], wherein R, R' and R'' are H or defined alkyl groups, such as Me, Et, nPr, iPr, nBu, iBi, sBu or tBu; the abbreviation "$N^{R,R'}$-fmd" or $N^R$-fmd when $R=R'$ refers to the formidinate ligand [R—N—C(H)=N—R'], wherein R and R' are defined alkyl groups, such as Me, Et, nPr, iPr, nBu, iBi, sBu or tBu. Collectively, a ligand selected in the amidinate family is abbreviated "AMD".

i)
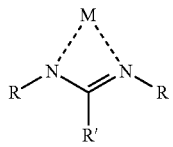
Amidinate ligand ii)
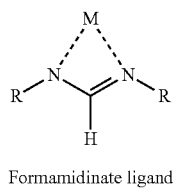
Formamidinate ligand

The standard abbreviations of the elements from the periodic table of elements are used herein. It should be understood that elements may be referred to by these abbreviations (e.g., Mn refers to manganese, Si refers to silicon, C refers to carbon, etc.). Additionally, Group 3 refers to Group 3 of the Periodic Table (i.e., Sc, Y, La, or Ac). Similarly, Group 4 refers to Group 4 of the Periodic Table (i.e., Ti, Zr, or Hf) and Group 5 refers to Group 5 of the Periodic Table (i.e., V, Nb, or Ta).

Any and all ranges recited herein are inclusive of their endpoints (i.e., x=1 to 4 or x ranges from 1 to 4 includes x=1, x=4, and x=any number in between), irrespective of whether the term "inclusively" is used.

Please note that the films or layers deposited, such as silicon oxide or silicon nitride, may be listed throughout the specification and claims without reference to their proper stoichiometry (i.e., $SiO_2$, $SiO_3$, $Si_3N_4$). The layers may include pure (Si) layers, carbide ($Si_oC_p$) layers, nitride ($Si_kN_l$) layers, oxide ($Si_nO_m$) layers, or mixtures thereof, wherein k, l, m, n, o, and p inclusively range from 1 to 6. For instance, silicon oxide is $Si_nO_m$, wherein n ranges from 0.5 to 1.5 and m ranges from 1.5 to 3.5. More preferably, the silicon oxide layer is $SiO_2$ or $SiO_3$. These films may also contain Hydrogen, typically from 0 at % to 15 at %. However, since not routinely measured, any film compositions given ignore their H content, unless explicitly stated otherwise.

A substrate is understood as the main solid material on which the film is deposited. It is understood that the film may be deposited on a stack of layers that are themselves on the substrate. Substrates are typically but not limited to wafers of silicon, glass, quartz, sapphire, GaN, AsGa, Ge. Substrates may be sheets, typically of metal, glass, organic materials like polycarbonate, PET, ABS, PP, HDPE, PMMA, etc. Substrates may be three-dimensional (3D) objects of similar materials. On silicon wafers, typical layers over the substrate may be Ge, SiGe, silicon oxide, silicon nitride, metals (such as Cu, Co, Al, W, Ru, Ta, Ti, Ni), metal silicides and alloys, metal nitrides such as TaN, TiN, VN, NbN, HfN, VN; carbon doped silica films, whether dense or porous, silicon carbo-nitride, amorphous carbon, boron nitride, boron carbonitride, organic materials such as spin-on-carbon, polyimides, photoresists and anti-reflective layers; metal oxides such as oxides of Ti, Hf, Zr, Ta, Nb, V, Mo, W, Al, and lanthanides. The substrates may have topographies like holes or trenches, typically having opening in the range of 5 nm to 100 μm, and usually between 20 nm and 1 μm, and aspect ratio of up to 1:1000, more usually in the range of 1:2 to 1:100.

BRIEF DESCRIPTION OF THE FIGURES

For a further understanding of the nature and objects of the present invention, reference should be made to the following detailed description, taken in conjunction with the accompanying FIGURE wherein:

FIGURE is a Gas Chromatographic spectrum of the perhydropolysilazane oil of the Example.

DESCRIPTION OF PREFERRED EMBODIMENTS

Silicon-containing film forming compositions are disclosed comprising short chain (Si ranging from 3 to 10) oligosilazanes having at least a trisilylamine backbone selected from the family of:

(1) $[(SiR_3)_2NSiH_2]_n—NL_{3-n}$, with n=2 or 3
(2) $(SiH_3)_2NSiH_2—O—SiH_2N(SiH_3)_2$
(3) $(SiR'_3)_2N—SiH_2—N(SiR'_3)_2$
(4) $[(SiR_3)_2NSiH_2]_m—NH_{2-m}—C≡N$, with m=1 or 2 in which
each R is independently selected from H, a dialkylamino group having the formula $—NR^1R^2$, or an amidinate;
each R' is independently selected from H, a dialkylamino group having the formula $—NR^1R^2$, or an amidinate, with the provision that all R' are not H
$R^1$ and $R^2$ are independently selected from H or a C1-C12 hydrocarbyl group with the provision that $R^1$ and $R^2$ cannot be simultaneously equal to H, and that if $R^1$ is H, then $R^2$ is a $C_2$ hydrocarbyl group or larger,
$NR^1R^2$ may form a N-containing heterocyclic ligand, and
L is selected from H or a $C_1$-$C_6$ hydrocarbyl group Preferred embodiments of the above compounds include:
A molecule of Family (1) in which all R=H, L=H and n=2: $[(SiH_3)_2NSiH_2]_2NH$
A molecule of Family (1) in which all R=H, L=a $C_1$-$C_6$ hydrocarbyl group and n=2: $[(SiH_3)_2NSiH_2]_2NL$
The above molecule in which L is selected from methyl, ethyl, isopropyl, n-propyl, tertiarybutyl, sec-butyl, n-butyl, hexyl, vinyl, allyl,
A molecule of Family (1) in which all R=H and n=3: $[(SiH_3)_2NSiH_2]_3N$
A molecule of Family (3) in which all except one R'=H and one R' is $NR^1R^2$, as defined above: $(SiH_3)_2N—SiH_2—N(SiH_3)(SiH_2N(R^1R^2))$
The above molecule in which $R^1=R^2=Et$
The above molecule in which $R^1=R^2=iPr$
The above molecule in which $R^1=R^2=Me$
The above molecule in which $R^1=Me$ and $R^2=Et$ The above molecule in which $R^1=R^2=tBu$
The above molecule in which $R^1=R^2=n-Bu$
The above molecule in which $R^1=R^2=secBu$
The above molecule in which $R^1=H$ and $R^2=tBu$
The above molecule in which $NR^1R^2$ is pyrrole, pyrrolidine, piperidine, imidazole or azidrine
The molecule of Family (4) being $[(SiH_3)_2NSiH_2]_2N—C\equiv N$
The molecule of Family (4) being $[(SiH_3)_2NSiH_2]—NH—C\equiv N$ Furthermore, the invention comprises the synthesis of compounds of families (1), (2), (3) and (4) from the following synthesis processes:

Family 1

(1) From the reaction of $(SiR_3)_2NSiH_2—X$, X being selected from Cl, Br, I, SCN or NCO, with a primary amine $NH_2L$ according to the reaction:

$$n(SiR_3)_2NSiH_2—X + NH_2L \rightarrow [(SiR_3)_2NSiH_2]_n—NL_{3-n} + (n+1)NH_3LX \text{ (salt)}$$

The reaction being preferably carried in an anhydrous and aprotic solvent or solvent mixture, such as but not limited to a $C_3$-$C_{24}$ hydrocarbon solvent, toluene, benzene, diethylether, acetonitrile, or tetrahydrofuran (THF).
The reaction being carried at a temperature between $-40°$ C. and $100°$ C., preferably at room temperature.
Optionally, the formed salt being filtered from the reaction mixture and the components of the remaining liquid composition being separated by distillation.
Optionally, the compound of family (1) being purified by distillation to reach an assay of >98%, more preferably or >99%, and even more preferably >99.5%, which is typical of semiconductor grade precursors
Optionally, the product of family (1) may be further treated to reduce the content of dissolved $NH_3LX$ salts, for instance by exposing the product to a solid adsorbent such as activated carbon, dried Amberlyst resin or other such ion exchange resin.
Optionally, the product may be filtered to reach specifications that are typical of products used in the semiconductor industry
the $(SiR_3)_2NSiH_2—X$ reactant may be synthesized as disclosed in co-pending US Pat. App. Pub. No. 2015/0376211, more particularly by $SnX_4 + N(SiR_3)_3 \rightarrow N(SiR_3)_2(SiR_2X) + SnX_2\downarrow + HXI$, wherein X is Cl, Br, or I (see *J. Chem. Soc. Dalton Trans.* 1975, p. 1624). Alternatively, dihalosilane [$SiR_2X_2$, wherein X is Cl, Br, or I] and monohalosilane [$SiR_3X$, wherein X is Cl, Br, or I] may be introduced continuously in the gas phase in a 1/20 to 1/4 ratio and at room temperature with 400 sccm of $NH_3$ in a flow-through tubular reactor as described by Miller in U.S. Pat. No. 8,669,387. The reaction of $NH_3$ with 2 equivalents of monohalosilane produces mostly disilylamine (DSA). DSA then reacts with the dihalosilane to form $(SiH_3)_2—N—SiH_2X$ and HX, wherein X is Cl, Br, or I. One of ordinary skill in the art would recognize that the reaction may take place in one or two steps (first forming DSA from the monohalosilane and $NH_3$ and second adding dihalosilane) or in one step (combining the monohalosilane, dichlorosilane, and $NH_3$ in one step).

(2) From the direct dehydrogenative coupling reaction of $(SiR_3)_2NSiH_3$ with $NH_2L$ in the presence of a catalyst, as described in U.S. Pat. App. Pub. No. 2015/0094470, according to the reaction:

$$n(SiR_3)_2NSiH_3 + NH_2L \rightarrow [(SiR_3)_2NSiH_2]_n—NL_{3-n} + H_2$$

The reaction being carried or neat or in an aprotic solvent such as, but not limited to a C3-C24 hydrocarbon solvent, toluene, benzene, diethylether, acetonitrile, or THF.
The reaction being carried at a temperature between room temperature and $150°$ C., preferably at $30$-$60°$ C.
Optionally, the catalyst being filtered from the reaction mixture and the components of the remaining liquid composition being separated by distillation.
Optionally, the reaction mixture being treated with an agent to de-activate the catalyst, selected but not limited to a tertiary amine or a coordinant compound such as $XNR_4$ (X=F, Cl, Br, I; R=alkyl), R—CN, $R_2S$, or $PR_3$.
Optionally, the compound of family (1) being purified by distillation to reach an assay of >98%, more preferably or >99%, and even more preferably >99.5%, which is typical of semiconductor grade precursors
Optionally, the product may be filtered to reach specifications that are typical of products used in the semiconductor industry.

Family 2

(3) From the reaction of $(SiH_3)_2NSiH_2—X$, wherein X is selected from Cl, Br, I, SCN NCO, or a $NR^1R^2$ group, and $NR^1R^2$ as defined above, with a $H_2O$ reactant according to the reaction:

$$2(SiH_3)_2NSiH_2—X + H_2O \rightarrow (SiH_3)_2NSiH_2—O—SiH_2N(SiH_3)_2 + 2HX$$

The reaction being preferably carried in an anhydrous or aprotic solvent or solvent mixture, such as but not limited to a $C_3$-$C_{24}$ hydrocarbon solvent, toluene, benzene, diethylether, acetonitrile, or THF.
The $H_2O$ being added slowly into the silane containing composition to maintain a constant excess of the silane moiety throughout the reaction
The reaction being carried at a temperature between $-40°$ C. and $100°$ C., preferably between $-20°$ C. to room temperature.
Optionally the water being added subsurface as vapor in a carrier gas
Optionally the water being added diluted in a polar non protic solvent, typically from 1% to 50%, more preferably from 5% to 30%
Optionally, and preferentially when X is a halogen, the reaction mixture comprising a halide scavenger, such as but not limited to pyridine, trialkylamine, in a quantity higher than the HX expected release on a molar basis. The halide scavenger may be used as the solvent. The reaction mixture may then be filtered to remove the HX-scavenger salt formed prior to the final product separation.
Optionally, the compound of family (2) being purified by vacuum distillation to reach an assay of >98%, more preferably or >99%, and even more preferably >99.5%, which is typical of semiconductor grade precursors
Optionally, the product of family (2) may be further treated to reduce the content of dissolved salts, for instance by exposing the product to a solid adsorbent such as activated carbon, dried Amberlyst resin or other such ion exchange resin.
Optionally, the product may be filtered to reach specifications that are typical of products used in the semiconductor industry.

Family 3

Compounds of Family 3 are preferentially synthesized from the direct reaction of $(SiH_3)_2N—SiH_2—N(SiH_3)_2$ (BDSASi) with an amine by dehydrogenative coupling, according to the same protocol as described in U.S. Pat. App. Pub. No. 2015/0094470.

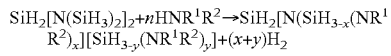

with x=0 to 3, y=1 to 3

The reaction being carried neat or in an aprotic solvent such as, but not limited to a C3-C24 hydrocarbon solvent, toluene, benzene, diethylether, acetonitrile, or THF.

The reaction being carried at a temperature between room temperature and 150° C., preferably at 30-60° C.

Optionally, the catalyst being filtered from the reaction mixture and the components of the remaining liquid composition being separated by distillation.

Optionally, the reaction mixture being treated with an agent to de-activate the catalyst, selected but not limited to a tertiary amine or a coordinant compound such as $XNR_4$ (X=F, Cl, Br, I; R=alkyl), R—CN, $R_2S$, $PR_3$.

Optionally, the compound of family (3) being purified by distillation to reach an assay of >98%, more preferably or >99%, and even more preferably >99.5%, which is typical of semiconductor grade precursors Optionally, the product may be filtered to reach specifications that are typical of products used in the semiconductor industry.

the $(SiR_3)_2NSiH_2$—X reactant may be synthesized as disclosed in U.S. Pat. App. App. No. 62/432,592, more particularly by mixing trisilylamine with a catalyst, such as $B(C_6F_5)_3$, $BPh_3$, $PdCl_2$, $Co_2(CO)_8$, or Zeolite Y (H) Si:Al, without a $NH_3$ reactant or heat.

Family 4

From the reaction of $(SiR_3)_2NSiH_2$—X, X being selected from Cl, Br, I, SCN or NCO, with the cyanamine group $H_2N$—C≡N, according to the reaction:

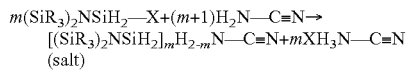

The reaction being preferably carried in an anhydrous and aprotic solvent or solvent mixture, such as but not limited to a $C_3$-$C_{24}$ hydrocarbon solvent, toluene, benzene, diethylether, acetonitrile, or THF.

The reaction being carried at a temperature between −40° C. and 100° C., preferably at room temperature.

Optionally, the formed salt being filtered from the reaction mixture and the components of the remaining liquid composition being separated by distillation.

Optionally, the compound of family (4) being purified by vacuum distillation to reach an assay of >98%, more preferably or >99%, and even more preferably >99.5%, which is typical of semiconductor grade precursors Optionally, the product of family (4) may be further treated to reduce the content of dissolved $XH_3N$—C≡N salts, for instance by exposing the product to a solid adsorbent such as activated carbon, dried Amberlyst resin or other such ion exchange resin.

To ensure process reliability, the disclosed Si-containing film forming compositions may be purified by continuous or fractional batch distillation prior to use to a purity ranging from approximately 95% w/w to approximately 100% w/w, preferably ranging from approximately 98% w/w to approximately 100% w/w. One of ordinary skill in the art will recognize that the purity may be determined by H NMR and gas or liquid chromatography with mass spectrometry. The Si-containing film forming composition may contain any of the following impurities: halides ($X_2$), trisilylamine, monohalotrisilylamine, dihalotrisilylamine, $SiH_4$, $SiH_3X$, $SnX_2$, $SnX_4$, HX, $NH_3$, $NH_3X$, monochlorosilane, dichlorosilane, alcohol, alkylamines, dialkylamines, alkylimines, THF, ether, pentane, cyclohexane, heptanes, or toluene, wherein X is Cl, Br, or I. Preferably, the total quantity of these impurities is below 0.1% w/w. The purified composition may be produced by recrystallisation, sublimation, distillation, and/or passing the gas or liquid through a suitable adsorbent, such as a 4 A molecular sieve or a carbon-based adsorbent (e.g., activated carbon).

The concentration of each solvent (such as THF, ether, pentane, cyclohexane, heptanes, and/or toluene), in the purified mono-substituted TSA precursor composition may range from approximately 0% w/w to approximately 5% w/w, preferably from approximately 0% w/w to approximately 0.1 w/w. Solvents may be used in the precursor composition's synthesis. Separation of the solvents from the precursor composition may be difficult if both have similar boiling points. Cooling the mixture may produce solid precursor in liquid solvent, which may be separated by filtration. Vacuum distillation may also be used, provided the precursor composition is not heated above approximately its decomposition point.

The disclosed Si-containing film forming composition contains less than 5% v/v, preferably less than 1% v/v, more preferably less than 0.1% v/v, and even more preferably less than 0.01% v/v of any of its mono-, dual- or tris-, analogs or other reaction products. This embodiment may provide better process repeatability. This embodiment may be produced by distillation of the Si-containing film forming composition.

Purification of the disclosed Si—Containing film forming composition may also produce concentrations of trace metals and metalloids ranging from approximately 0 ppbw to approximately 500 ppbw, and more preferably from approximately 0 ppbw to approximately 100 ppbw. These metal or metalloid impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), Vanadium (V) and Zinc (Zn). The concentration of X (where X=Cl, Br, I) in the purified mono-substituted TSA precursor composition may range between approximately 0 ppmw and approximately 100 ppmw and more preferably between approximately 0 ppmw to approximately 10 ppmw.

Optionally, the product may be filtered to reach specifications that are typical of products used in the semiconductor industry.

Any of the compositions comprising any of the products from Families (1) through (4) may be used for the chemical vapor phase deposition (CVD) of silicon containing thin films for applications in the semiconductor, flat panel display, photovoltaic, and more generally for silicon based coatings. It is understood that the term "CVD" encompasses all embodiments in which a precursor is brought in a vapor phase in contact with a substrate on which the silicon thin film is to be deposited. As such, the term CVD may mean low pressure chemical vapor deposition (LPCVD), sub-atmospheric chemical vapor phase deposition (SA-CVD), atmospheric chemical vapor deposition (AP-CVD), Flowable chemical vapor deposition (F-CVD), Atomic Layer Deposition (ALD), Molecular Layer Deposition (MLD), Pulsed chemical vapor deposition (P-CVD), flow-modulated chemical vapor deposition (FM-CVD). Each of these techniques may be assisted by precursor or reactant activation techniques such as in-situ plasma ("Plasma Enhanced", or PE), remote plasma (RP), hot wire (HW), and photons (UV).

The precursors of Families (1) through (4) may be used in conjunction with a co-reactant that would be typically selected from:
- $O_2$, $O_3$, $H_2O$, $H_2O_2$, HCOOH, $CO_2$, radicals, ions and mixtures thereof for the deposition of silicon oxide containing films
- $N_2$, $H_2$, $NH_3$, hydrazines, primary, secondary or tertiary amines, diamines, ethanolamine, radicals, ions and mixture thereof for the deposition of silicon nitride containing films The precursors of Families (1) through (4) may be used in conjunction with another metal or metalloid volatile precursor to deposit silicon containing films. Examples of such films include but are not limited to SiTiO, SiAlO, SiZrO, SiHfO, SiBO, SiPO, SiAsO, SiBPO, SiGeO, SiBN, SiAlN, SiTiN, CoSiN, NiSiN, TaSiN, WSiN, understanding that the composition does not take into account the potential low level carbon impurities, typically <5%, and preferably <2%, coming from the precursors and the ligands.

Multiple volatile precursors of virtually every element of the periodic table are published and available, and typically involve at least one of the following ligands or combination of ligands to achieve sufficient stability and volatility: Hydrogen, halides (Cl, Br, I, F), alkyls, alkoxy, dialkylamino, carbonyl, cyclopentadienyl and other dienes, diazadiene, amidinates, borohydrides, aminoboranes, isocyanates, acetoxy, alkylsiloxy, silyl, bis(trialkylsilyl)amide.

The compounds of families (1), (2) and (4), having a hydrolysable functional group like $NR^1R^2$, N—C≡N, or —Si—NH—Si are particularly suitable for ALD or PE-ALD of silicon oxide or silicon nitride based films, as they provide a reactive site for the precursors to react with the hydroxyl (—OH) or —$NH_2$ groups on the surface substrate and chemically bind to it. They also have a number of silicon atom>3, and are hence expected to yield a higher growth per cycle versus the existing molecules.

The compounds of all families are also particularly suitable for LPCVD, PECVD and FCVD owing to their high silicon content and structure that is close to a silicon nitride pre-ceramic.

These compounds have a rather low vapor pressure and are suitable for deposition by condensation (C-CVD) over a substrate (by maintaining the substrate at a temperature lower than the dew point of the precursor in the deposition equipment). The thermally condensed composition may then be further treated by exposure to an oxidizing atmosphere such as $O_2$, $O_3$, steam, or $H_2O_2$ vapors, mixtures and plasma thereof, at a temperature preferably between 0° C. and 900° C., more preferably between 300° and 800° C., possibly in several steps to avoid the re-evaporation of the composition on the substrate, in order to convert the condensed silazane composition to a silica film. Such processes are particularly useful to deposit a dielectric film in fine trenches or holes (gap fill).

Similarly, the film may be exposed to a nitriding atmosphere ($N_2$, $NH_3$, hydrazines, and plasma thereof) at a temperature preferably between 100° C. and 1100° C., more preferably between 300° and 900° C. for conversion of the short chain polysilazane precursor to large chain polysilazanes and SiN pre-ceramics.

The compounds of families 1 through 4, and preferably the fully C-free compounds of family 1 and 2 may also be useful in formulation for liquid phase deposition such as spin coating, dip coating or spray coating, or as intermediates and ingredients for the synthesis of such formulations. As ingredients, these compounds may be polymerized to increase the molecular weight of the silazane, functionalized with amines or alcohols to convert some Si—H bond to more reactive alkoxy or alkylamino bonds. They may be reacted with compounds containing C=C, C=N or C=O insaturations to form Si—C bonds by hydrosilylation, preferably in the presence of a catalyst. They may be reacted with ammonia, amines or polyamines to create silazane bridges between Si atoms.

Example

The following example illustrates an experiment performed in conjunction with the disclosure herein. The example is not intended to be all inclusive and is not intended to limit the scope of disclosure described herein.

Inside a glove box, 0.35 g (2.7 mmol) of $(H_3Si)_2$—N—$SiH_2Cl$ (TSA-Cl)* was mixed with 0.39 g of Pentane. The mixture was added to 0.1 g (2.4 mmol) of Cyanamide ($H_2N$—CN) in 0.5 g of Ether. White precipitation occurred immediately. The solution was filtered twice. Both times the initially clear filtrate turned hazy.

The presumed reaction is $2(SiH_3)_2NSiH_2$—Cl+$4H_2N$—CN→$[(SiH_3)_2NSiH_2]_2$-NCN+$2H_2N$—CN*HCl Gas Chromatographic (GC) analysis indicated the presence of monochlorosilane, ether and pentane, unreacted TSA-Cl, $(SiH_3)_2NSiH_2$N—C≡N—$SiH_3$, or $[(SiH_3)_2NSiH_2]_2$—N—C≡N ($TSA_2$-Cyanamide). There were many other smaller, unidentified peaks. The GC spectrum of the mixture is shown in the FIGURE. One of ordinary skill in the art will recognize that a suitable distillation column would be capable of isolating the $TSA_2$-Cyanamide from the $(H_3Si)_2$—N—$SiH_2$—NCN—$SiH_3$.

having an initial ~85% purity as determined by GC. Applicants believe that the monochlorosilane shown in the FIGURE was an impurity in the TSA-Cl reactant.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

We claim:

1. A silicon-containing film forming composition comprising a precursor selected from the group consisting of:

$[(SiR_3)_2NSiH_2]_m$—$NH_{2-m}$—C≡N, with $m$=1 or 2;   (a)

$[(SiR_3)_2NSiH_2]_n$—$NL_{3-n}$, with $n$=2 or 3;   (b)

$(SiH_3)_2NSiH_2$—O—$SiH_2N(SiH_3)_2$; and   (c)

$(SiR'_3)_2N$—$SiH_2$—$N(SiR'_3)_2$;   (d)

wherein
- each R is independently selected from H, a dialkylamino group having the formula $NR^1R^2$, or an amidinate,
- Each R' is independently selected from H, a dialkylamino group having the formula $NR^1R^2$, or an amidinate, with the provision that all R' are not H, $R^1$ and $R^2$ are independently selected from H or a C1-C12 hydrocarbyl group, with the provision that $R^1$ and $R^2$ cannot be simultaneously equal to H, and that if $R^1$ is H, then $R^2$ is a $C_2$-C12 hydrocarbyl group, and NR' $R^2$ may together form an N-containing heterocyclic ligand, and L is selected from H or a $C_1$-$C_6$ hydrocarbyl group.

2. The silicon-containing film forming composition of claim 1, wherein the precursor is $(SiH_3)_2N$—$SiH_2$—$N(SiH_3)(SiH_2NR^1R^2)$, $(SiH_3)_2NSiH_2$—O—$SiH_2N(SiH_3)_2$, $[(SiH_3)_2NSiH_2]$—NH—C≡N, or $[(SiH_3)_2NSiH_2]_2N$—C≡N.

3. The silicon-containing film forming composition of claim 1, wherein the precursor is $[(SiH_3)_2NSiH_2]_2NH$ or $[(SiH_3)_2NSiH_2]_3N$.

4. The silicon-containing film forming composition of claim 1, wherein the precursor is $(SiH_3)_2N$—$SiH_2$—$N(SiH_3)(SiH_2NMe_2)$, $(SiH_3)_2N$—$SiH_2$—$N(SiH_3)(SiH_2NEt_2)$, $(SiH_3)_2N$—$SiH_2$—$N(SiH_3)(SiH_2NEtMe)$, $(SiH_3)_2N$—$SiH_2$—$N(SiH_3)(SiH_2NiPr_2)$, $(SiH_3)_2N$—$SiH_2$—$N(SiH_3)(SiH_2NtBu_2)$, $(SiH_3)_2N$—$SiH_2$—$N(SiH_3)(SiH_2NnBu_2)$, $(SiH_3)_2N$—$SiH_2$—$N(SiH_3)(SiH_2NsecBu_2)$, or $(SiH_3)_2N$—$SiH_2$—$N(SiH_3)(SiH_2NHtBu)$.

5. A method of deposit a silicon-containing film on a substrate by a chemical vapor deposition method, the method comprising
introducing into a reactor containing a substrate a vapor including the Si-containing film forming composition of claim 1;
depositing at least part of the precursor onto the substrate to form the silicon-containing film on the substrate using a chemical vapor deposition process.

6. The method of claim 5, wherein the chemical vapor deposition method is an atomic layer deposition process or a plasma enhanced atomic layer deposition process.

7. The method of claim 5, wherein the silicon-containing film is a silicon oxide film.

8. The method of claim 5, wherein the silicon-containing film is a silicon nitride film.

9. The method of claim 5, wherein the substrate is a silicon wafer.

10. The method of claim 5, wherein the substrate is glass.

11. The method of claim 5, wherein the substrate is an organic material.

* * * * *